United States Patent [19]

Nicolaou et al.

[11] Patent Number: 5,274,141
[45] Date of Patent: Dec. 28, 1993

[54] DESIGNED QUINONE- AND HYDROQUINONE-CONTAINING CYCLIC ENEDIYNEOLS AND ENEDIYNEONES HAVING DNA CLEAVING AND CYTOTOXIC PROPERTIES

[75] Inventors: Kyriacos C. Nicolaou, La Jolla, Calif.; Aijun Liu, Nutley, N.J.

[73] Assignee: The Scripps Research Institute, La Jolla, Calif.

[21] Appl. No.: 938,756

[22] Filed: Sep. 1, 1992

[51] Int. Cl.$^5$ .................. C07C 50/06; C07C 50/14; C07C 50/20
[52] U.S. Cl. .................. 552/220; 536/25.4; 552/298; 552/299
[58] Field of Search .............. 552/299, 220, 298; 536/25.4; 514/680, 681, 729, 732

[56] References Cited

U.S. PATENT DOCUMENTS 5,136,099 8/1992 Skokotas et al. .................. 568/327
5,183,942 2/1993 Nicolaou et al. .................. 568/375

OTHER PUBLICATIONS

Nicolaou et al., *J. Am. Chem. Soc.*, 110:4866–4868 (1988).

*Primary Examiner*—Marianne M. Cintins
*Assistant Examiner*—Kimberly J. Kestler
*Attorney, Agent, or Firm*—Dressler, Goldsmith, Shore & Milnamow, Ltd.

[57] ABSTRACT

Quinone- and hydroquinone-containing cyclic enediyneols and enediyneones having 10-carbon atoms in the enediyne-containing ring that cleave DNA are disclosed, as are methods of making and using the same.

14 Claims, 1 Drawing Sheet

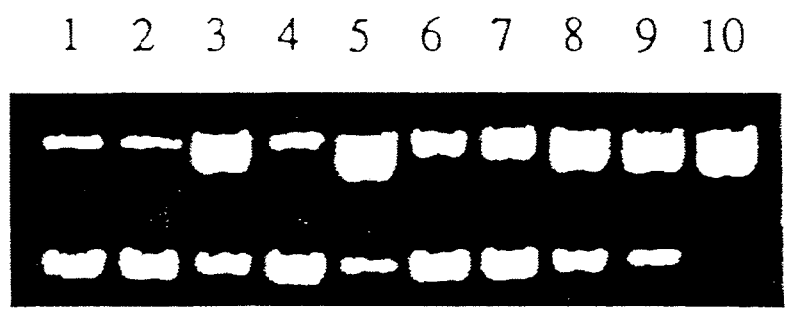

DESIGNED QUINONE- AND HYDROQUINONE-CONTAINING CYCLIC ENEDIYNEOLS AND ENEDIYNEONES HAVING DNA CLEAVING AND CYTOTOXIC PROPERTIES

GOVERNMENTAL RIGHTS

This invention was made with support from the United States Government under National Institutes of Health Grant CA 46446, and the United States Government has certain rights in the invention.

DESCRIPTION

1. Technical Field

The present invention relates to novel DNA-cleaving and antitumor compounds, and more specifically to a group of quinone- or hydroquinone-containing cyclic enediyneols and enediyneones having ten carbons in the enediyne ring.

2. Background Art

Natural products have been capturing the interest and imagination of isolation, synthetic, and medicinal chemists for a very long time due to their fascinating structures and biological activities. Man-designed molecules ("designer molecules") with predefined chemical and biological properties could enrich and complement this arsenal of substances, and sharpen the capability of chemistry to deliver biologically and therapeutically useful compounds.

Described herein are the design, synthesis, chemical and biological actions of novel designer molecules with DNA cleaving and antitumor properties; for some recent examples of designed DNA-cleaving molecules, see: (a) Nicolaou et al., *J. Am. Chem. Soc.*, 110:4866, 7247 (1988); (b) Nicolaou et al., *Angew. Chem. Int. Ed. Engl.*, 28:1272 (1989); (c) Povsic et al., *J. Am. Chem. Soc.*, 111:3059 (1989); (d) Hertzberg et al., *J. Am. Chem. Soc.*, 104:313 (1982); (e) Moser et al., *Science*, 238:645 (1987); (f) Corey et al., *J. Am. Chem. Soc.*, 111:8523 (1989); (g) Pyle et al., *J. Am. Chem. Soc.*, 111:4520 (1989); (h) Sigman, *J. Am. Chem. Soc.*, 111:4941 (1989); (i) Ohno et al., *J. Am. Chem. Soc.*, 112:838 (1990); (j) Danishefsky, *J. Org. Chem.*, 54:2781 (1989); Nicolaou et al., *Angew. Chem. Int. Ed. Engl.*, 103:1032 (1991); and allowed U.S. patent application Ser. No. 07/788,161, filed Nov. 5, 1991.

In addition to the man-made DNA cleaving compounds, naturally occurring enediyne compounds have also been reported and studies. Included among the naturally occurring enediynes are calicheamicin and esperamicin that have substantially identical aglycon portions but different sugar portions [(a) Lee et al., *J. Am. Chem. Soc.*, 109:3464, 3466 (1987); (b) Nicolaou et al., *J. Am. Chem. Soc.*, 110:7247 (1988); (c) Hawley et al., *Proc. Natl. Acad. Sci. USA*, 86:1105 (1989); (d) Golik et al., *J. Am. Chem. Soc.*, 109:3461, 3462 (1987)] and neocarzinostation that also contains sugar-derivative side chains [(a) Edo et al., *Tetrahedron Lett.*, 26:331 (1984); (b) Chin et al. *Biochemistry*, 27:8106 (1988); (c) Lee et al., *Biochemistry*, 28:1019 (1989)].

BRIEF SUMMARY OF THE INVENTION

The invention contemplates novel DNA-cleaving, antibiotic and antitumor compounds that contain a quinoid or hydroquinoid ring fused to a 10-membered enediyne ring that includes a hydroxyl or keto (oxo) group on a carbon atom adjacent to a triple bond. General structural formulas for a quinoid- or hydroquinoid-containing enediyneol compound and enediyneone compound are shown below as structural Formula I.

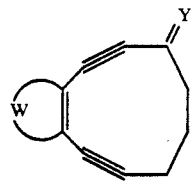

wherein =Y is =O or —OH and —H, and

W together with the carbon atoms of the depicted, intervening vinylene group forms a benzoquinoidal, naphthoquinoidal or anthraquinoidal ring system or the corresponding hydroquinoidal form thereof, with the proviso that when W forms a corresponding hydroquinoidal ring system, =Y is —OH and —H.

A preferred group of compounds of structural Formula I are the compounds of structural Formulas II and III, below,

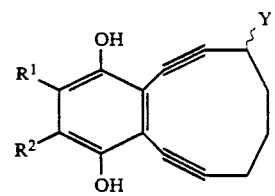

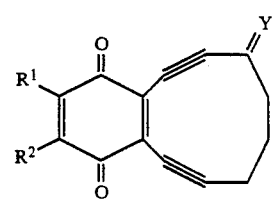

wherein =Y is =O or —OH and —H, and $R^1$ and $R^2$ are the same or different and are selected from the group consisting of hydrogen, $C_1$-$C_6$ alkyl and $C_1$-$C_6$ alkoxy.

It is preferred that $R^1$ and $R^2$ be the same and $C_1$-$C_6$ alkyl. A compound wherein $R^1$ and $R^2$ are both methyl is most preferred.

A pharmaceutical composition that contains a before-defined compound present in a DNA-cleaving, or tumor growth-inhibiting amount dissolved or dispersed in a physiologically tolerable diluent is also contemplated.

A method utilizing a before-discussed composition containing a compound of structural Formula I is also contemplated. Here, DNA to be cleaved or target tumor cells whose growth is to be inhibited are contacted with a compound of Formula I, preferably in a before-described composition. That contact is maintained for a time period sufficient for the desired result to be effected. Multiple administrations of the composition are also contemplated.

BRIEF DESCRIPTION OF THE DRAWINGS

In the drawings forming a portion of this disclosure,

FIG. 1 is a photograph of an ethidium bromide stained 1 percent agarose electrophoresis gel o that illustrates the cleavage of φX174 form I DNA (100 μM base pairs) by Compounds 7, 8, 9, 10 and 12 at 50-5000

μM after 15 hours at 37° C. at a pH value of 7.4 in 50 μM Tris HCl buffer. Lane 1 shows the DNA alone as control. Lanes 2-10 correspond to the following: Lane 2: Compound 12 (100 μM); Lane 3: Compound 10 (100 μM); Lane 4: Compound 7 (100 μM); Lane 5: Compound 8 (100 μM); Lanes 6-10: Compound 9 (50, 100, 500, 1000 and 5000 μM). Forms I, II and III shown to the left of the photograph show the relative migrations of supercoiled (form I) relaxed (form II) and linear (form III) DNA, respectively.

DETAILED DESCRIPTION OF THE INVENTION

I. Introduction

The present invention relates to compounds, compositions and methods for cleaving DNA and thereby killing targeted cells such as tumor cells. Three related general types of compounds are contemplated.

The first is a quinoidal enediyneol that contains ten carbon atoms in the enediyneol ring such as Compound 8. These compounds can themselves cleave DNA and are cytotoxic to cancer cells such as Molt-4 leukemia cells.

The second is a hydroquinoidal enediyneol that can be prepared from an above quinoidal enediyneol and also contains ten carbon atoms in the enediyneol ring such as Compound 9. These compounds also cleave DNA, but are not particularly cytotoxic. However, the hydroquinone is readily oxidized in vivo. These compounds can therefore be viewed as prodrugs for a quinoidal enediyneol compound.

The third compound type is a quinoidal enediyneone. This type of compound can be prepared from a quinoidal enediyneol, cleaves DNA and is cytotoxic to cancer cells such as Molt-4 cells.

II. The Compounds

A compound contemplated by the present invention corresponds to structural Formula I, below,

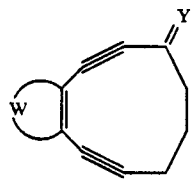

I wherein =Y is =O or —OH and —H, and
W together with the carbon atoms of the depicted, intervening vinylene group forms a benzoquinoidal, naphthoquinoidal or anthraquinoidal ring system or the corresponding hydroquinoidal form thereof, with the proviso that when W forms a corresponding hydroquinoidal ring system, —Y is —OH and —H.

A preferred group of compounds of structural Formula I are the compounds of structural Formulas II and III, below,

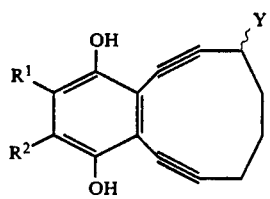

II

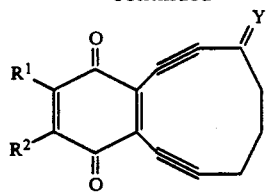

III wherein =Y is =O or —OH and —H, and
$R^1$ and $R^2$ are the same or different and are selected from the group consisting of hydrogen, $C_1$-$C_6$ alkyl and $C_1$-$C_6$ alkoxy. Here, W of structural Formula I formed a hydrobenzoquinone or benzoquinone, respectively.

A preference as to $R^1$ and $R^2$ is that both be the same group; i.e., if $R^1$ is $C_1$-$C_6$ alkyl, $R^2$ is $C_1$-$C_6$ alkyl. The basis for this preference is ease of chemical synthesis in that if $R^1$ and $R^2$ are different from each other, mixtures of isomers can be formed that could require separation and loss of overall yield, whereas if $R^1 = R^2$ there would be no mixtures.

The hydroxyl of the 10-membered ring of Formula I or that of the other formulas herein, where =Y is —OH and —H, can be above ($\beta$) or below ($\alpha$) the plane of that ring as shown, as can the hydrogen atom that is not shown. Those $\alpha$ and $\beta$ configurations are indicated by a wavy line in Formula II and formulas elsewhere herein. In addition, where a hydrogen is not needed to show stereochemistry or to complete a group such as a methylene or a hydroxyl group, that hydrogen is not shown following usual conventions.

Exemplary compounds, in addition to the benzoquinoids shown before, wherein W together with the carbon atoms of the depicted, intervening vinylene group forms naphthoquinoidal or anthraquinoidal ring systems or their corresponding hydroquinoidal forms are illustrated below by structural Formulas IV-IX, wherein =Y is as before-defined.

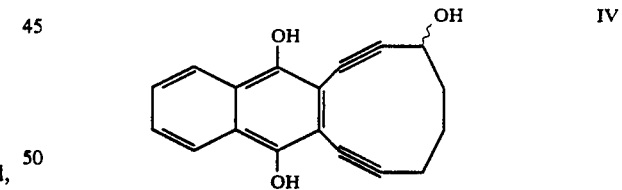

IV

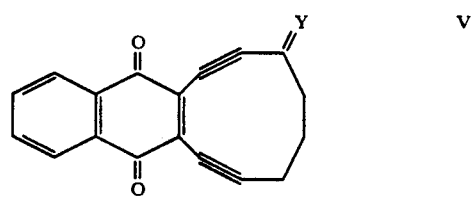

V

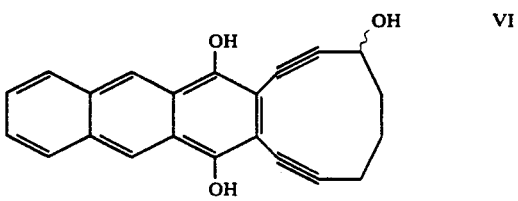

VI

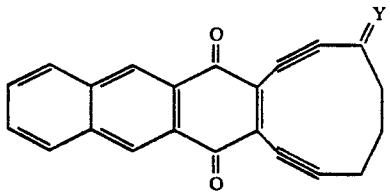

VII

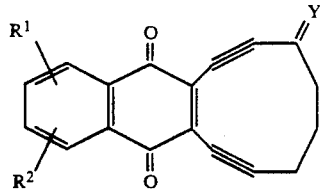

XI

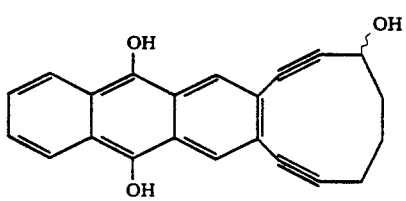

VIII

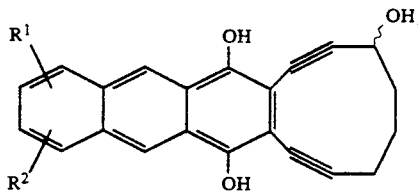

XII

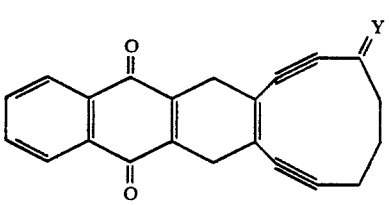

IX

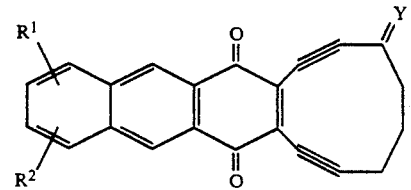

XIII

The W quinoidal or hydroquinoidal ring system can have bonded to it, at various positions (other than those required for the fusion to the depicted vinylene carbon atoms) hydrogen or a variety of substituents. Exemplary substituents include methyl, ethyl, isopropyl, n-propyl, isobutyl, sec-butyl, t-butyl, hexyl, and cyclohexyl ($C_1$-$C_6$ alkyl) and methoxy, ethoxy, propoxy, butoxy, iso-butoxy, cyclopentyloxy, and cyclohexyloxy ($C_1$-$C_6$ alkoxy).

For ease of synthesis, because of the formation of isomeric products, it is preferred that a compound of Formula I include a plane of symmetry that can be drawn bisecting the vinylene bond and any quinoid of hydroquinoid ring system W bonded thereto, with the α or β stereochemistry of the hydroxyl group being neglected. Similarly, any substituents present on a quinoid or hydroquinoid ring system W are preferably symmetrically substituted about the depicted vinylene bond of Formula I.

Of the above W ring systems, a benzo ring is preferred. A substituted benzo ring is also contemplated, as noted for a compound of Formulas II and III, as are other substituted ring systems W, and substituents can be bonded at the remaining positions not utilized in the fusion to the depicted vinylene carbons. Structural Formulas X-XV for further exemplary compounds are illustrated below, wherein =Y and $R^1$ and $R^2$ are as previously defined.

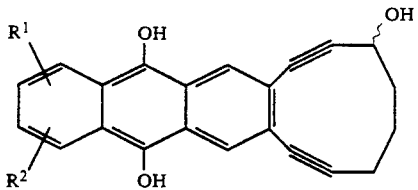

XIV

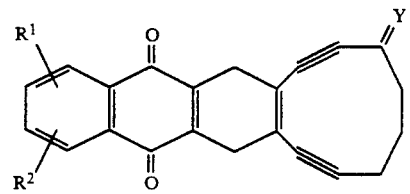

XV

Reference is made herein to the carbon atoms of the vinylene group of depicted structural formulas. Following modern theories, those carbon atoms from $sp^2$ bonds. Atoms in the quinoidal and hydroquinoidal W groups also form $sp^2$ bonds.

Thus, when W together with the intervening carbon atoms of a depicted vinylene group form a quinoidal or hydroquinoidal ring system the bonding of those carbon atoms of the depicted vinylene group remains $sp^2$. Nevertheless, usual structural formulas for quinoidal or hydroquinoidal compounds that utilize alternating double and single bonds can show a single bond rather than a double bond at the position occupied by a depicted vinylene group.

In view of the fact that the hybridization of the carbons of a depicted vinylene group remain $sp^2$, and such $sp^2$ hybridization rather than the presence of a vinylene group, per se, is what is of importance in the reactions of a compound of the invention, the absence of a "formalized", double bond in a written formula for a compound of Formula I is of no consequence.

In reviewing the above preferences it is seen that in particularly preferred practice, $R^1=R^2$ In addition, particularly preferred $R^1$ and $R^2$ groups are methyl. Structural formulas for the particularly preferred hydroquinoidal enediyneol of Formula II (Compound 9),

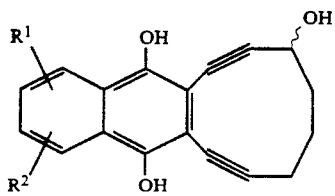

X the quinoidal enediyneol and quinoidal enediyneone of Formula III (Compounds 8 and 10, respectively), are shown below.

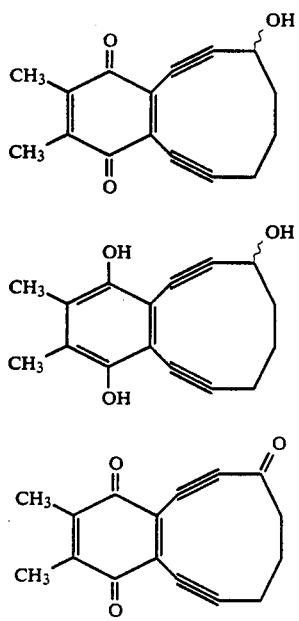

III. Syntheses

A compound of the invention is prepared readily. A detailed description of the preparation of exemplary benzoquinoid and hydroquinoid, preferred Compounds 8, 9 and 10 is provided in Scheme 1 and the adjoining text, hereinafter. The discussion that follows will therefore center on preparation of compounds where W together with the depicted vinylene group carbon atoms forms a naphthoquinoidal or anthraquinoidal ring system.

In a preferred method of synthesis, the portions of the molecule containing the triple bonds are added separately to a vicinyl-dihalohydroquinone portion as silyl-containing entities. The silyl groups of the resulting enediyne compound are then removed, and formed into a halide and an aldehyde, and are then linked to form a 10-membered hydroxyl-containing cyclic enediyne.

As noted earlier, it is preferred that the whole molecule be symmetrical with a plane of symmetry bisecting the vinylene group. In view of the fact that difficultly separable isomers can arise when $R^1$ and $R^2$ are not identical, it is also preferred that $R^1$ and $R^2$ be identical as noted before.

Notwithstanding the above preferences for a symmetrical compound and sameness of $R^1$ and $R^2$, asymmetric molecules are also contemplated. Such molecules are, however, less preferred because of the difficulties involved with separation of the various isomers that can be produced.

One starting material is a vicinyldihalohydroquinone. Such compounds are well known in the art, and can be prepared from their usually more available corresponding quinone forms by gentle reduction. For example, 2,3-dichloro-1,4-naphthoquinone, available from Aldrich Chemical Co., Inc., Milwaukee, Wis., can be reduced with a borohydride reagent or aqueous dithionite ion to form the corresponding hydroquinone. The vicinyl dihalide can be prepared from a quinone as is illustrated hereinafter or from a hydroquinone.

It is preferred that the vicinyl halo groups of the quinone or hydroquinone be the same halogen. That halogen can be a chloro, bromo, or iodo group, with iodo groups being preferred. Preferred vicinyl iodo compounds can be prepared from corresponding dichloro or dibromo compounds by an iodine exchange reaction.

Suitable $C_1$-$C_6$ alkylated vicinyl dihaloquinones and hydroquinones are also known in the art. Suitable $C_1$-$C_6$ dialkoxy vicinyl dihalohydroquinones can be prepared by $C_1$-$C_6$ alkylation of the corresponding quinonediols, followed by reduction of the oxo groups and then halogenation. For example, quinizarin (1,4-dihydroxyanthraquinone), also available from Aldrich, can be alkylated as with dimethyl sulfate, reduced as discussed before and then dihalogenated under standard conditions for aromatic compounds.

A suitable vicinyl dihalohydroquinone is then sequentially reacted and condensed with $HC\equiv CSiMe_3$ ($Me=CH_3$) and then with $HC\equiv C(CH_2)_4OSi^tBuMe_2$ ($^tBu=t$-butyl) to form a corresponding open chain enediyne whose triple bond-containing groups are protected with the above silyl groups. The above condensations are carried out by use of a Pd(O)-Cu(I) catalyst in a solvent such as benzene and in the presence of an excess of an amine such as di-isopropylamine.

The hydroquinone hydroxyls are then protected with a base insensitive protecting group other than a silyl group, with pivaloyl groups being preferred. A bis(pivaloyl) ester is thus formed.

The silyl protecting groups are then separately removed to form the respective acetylene- and hydroxyl termini. The acetylene hydrogen atom is replaced with a halogen, preferably an iodo group, and the hydroxyl group is gently oxidized to form an aldehyde, as with pyridinium chlorochromate (PCC). The 10-membered ring is then closed in the presence of an excess of $CrCl_2$ and a catalytic amount of $NiCl_2$ to form the hydroxyl-containing 10-membered ring enediyne.

Removal of the pivaloyl groups as with excess $LiAlH_4$ provides a quinone of structural Formula I, where $=Y$ is —OH and —H. The quinone form is recovered via a presumed air-sensitive corresponding hydroquinone precursor. Reaction of the quinone with a mild oxidant such as PCC in the presence of 4Å molecular sieves provides a compound of structural Formula I where $=Y$ is $=O$. On the other hand, reaction of that quinone with a reducing agent such as dithionite ion provides the hydroquinone form of a compound of structural Formula I where $=Y$ is —OH and —H.

IV. Pharmaceutical Compositions

A compound of structural Formula I is useful as a DNA cleaving agent, as are dynemicin A, calicheamicin, esperamicin and neocarzinostatin. A compound of the invention can also therefore be referred to as an "active agent" or "active ingredient". A compound of that structural formula can also be used to inhibit the growth of neoplastic cells as can those known compounds in that cytotoxicity toward tumor cells by those previously known compounds proceeds via DNA cleavage, at least in part. Thus, a pharmaceutical composition of a compound of structural Formula I is contemplated.

Cleavage of cell-free DNA can be assayed using the techniques described hereinafter as well as those described by Mantlo et al., *J. Org. Chem.*, 54:2781 (1989); Nicolaou et al., *J. Am. Chem. Soc.*, 110:7147 (1989); Nicolaou et al., *J. Am. Chem. Soc.*, 110:7247 (1988) or Zein et al., *Science*, 240:1198 (1988) and the citations therein.

A before-described compound can also be shown to undergo a Bergman cycloaromatization reaction in the presence of benzyl mercaptan, 1,4-cyclohexadiene or other hydrogen donor as discussed in Haseltine et al., *J. Am. Chem. Soc.*, 111:7638 (1989). This reaction forms a benzene-containing reaction product as is formed during DNA cleavage, and can be used as a co-screen to select more active compounds.

A pharmaceutical composition is thus contemplated that contains a before-described compound of the invention as active agent. A pharmaceutical composition is prepared by any of the methods well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier or diluent.

A carrier or diluent is a material useful for administering the active compound and must be "pharmaceutically acceptable" in the sense of being compatible with the other ingredients of the composition and not deleterious to the recipient thereof. Thus, as used herein, the phrases "physiologically tolerable" or "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Hack Publishing Co., Easton, Pa. (1980).

An active agent can also be administered in the form of liposomes. As is known in the art, liposomes are generally derived from phospholipids or other lipid substances. Liposomes are formed by monoor multilamellar hydrated liquid crystals that are dispersed in an aqueous medium. Any non-toxic, pharmaceutically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Ed., *Methods in cell Biology*, Vol. XIV, Academic press, New York, N.Y. (1976), p.33 et seq.

An active agent can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical composition described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A compound of the invention is present in such a pharmaceutical composition in an amount effective to achieve the desired result. For example, where in vitro cell-free DNA cleavage is the desired result, a compound of the invention can be utilized in an amount sufficient to provide a concentration of about 1.0 to about 10,000 micromolar ($\mu$M) with a DNA concentration of about 0.02 $\mu$g/mL. As a cytotoxic (antitumor) agent, an effective amount of a compound of the invention is about 0.1 to about 50 mg per kilogram of body weight or an amount sufficient to provide a concentration of about 0.01 to about 100 $\mu$g/mL to the bloodstream. In in vitro cytotoxicity assays, a compound of structural Formula I exhibits IC$_{50}$ values on the order of $10^{-4}$–$10^{-7}$ M, depending upon the cells assayed and compound utilized. Inasmuch as all of the above uses ultimately result from DNA cleavage, the above amounts of an active agent are referred to as DNA cleaving amounts.

V. Methods

A contemplated compound is useful in cleaving cell-free DNA, and also in inhibiting the growth (killing) of neoplastic tumor cells via DNA cleavage, and is utilized in a method for effecting such a result. Such a compound is typically utilized in a before-described composition.

In accordance with such a method, cell-free DNA to be cleaved or target neoplastic tumor cells to be killed are contacted in an aqueous medium with a compound of Formula I, preferably in a before-described composition that contains a contemplated compound of the invention (active ingredient) present in an amount effective or sufficient for such a purpose; i.e., in a DNA cleaving amount, dissolved or dispersed in a physiologically tolerable (pharmaceutically acceptable) diluent. That contact is maintained for a time sufficient for the desired result to be obtained; i.e., cell-free DNA cleaved, or neoplastic cell growth inhibited.

Where the desired result is carried out in vitro contact is maintained by simply admixing the cell-free DNA or target cells with the compound in an aqueous medium and maintaining them together under the appropriate conditions of temperature, pH, and the presence of nutrients for cell growth to occur; i.e., culture conditions, as for control, untreated cells. Thus, a single admixing and contacting is typically sufficient for in vitro purposes, whether the DNA is in cell-free form or within living cells.

The above method is also useful in vivo, as where a mammal such as a rodent like a rat, mouse, or rabbit, a farm animal like a horse, cow or goat, or a primate like a monkey, ape or human is treated. Here, contact of a compound and the cells to be killed via DNA cleavage is achieved by administration of the composition to the mammal by oral, nasal or anal administration or by introduction intravenously, subcutaneously or intraperitoneally. Thus, contact in vivo is achieved via the blood or lymph systems as the aqueous medium.

Although a single administration (admixture) and its resulting contact is usually sufficient to maintain the required contact and obtain a desired result in vitro, multiple administrations are typically utilized in vivo. Thus, because of a body's breakdown and excreting pathways, contact between an active agent and the target cells is typically maintained by repeated administration of a compound of the invention over a period of time such as days, weeks or months, or more, depending upon the target cells.

Thus, an aqueous medium can be a buffer system for cleaving cell-free DNA, a nutrient-containing culture medium as for cytotoxicity studies or a body fluid such as blood or lymph.

The time, temperature and pH value for maintenance can also be varied. For cleaving cell-free DNA, 0.5-2 days at a temperature of about 25°–50° C. and pH value of about 7–9 can be used. For DNA cleavage in cytotoxicity studies, tissue culture temperatures and pH values as are well known are used with maintenance times of about 0.5-4 days. For in vivo use, the host animal's body temperature, body fluid pH values and metabolism/catabolism/excretion control maintenance parameters.

Exemplary methods of the invention for cell-free DNA cleavage and in vitro cytotoxicity of cancer cell lines and normal cells are illustrated hereinafter.

VI. Results

Exemplary compounds 8-10 (shown previously) were targeted for synthesis for their novel structures and potential chemical and biological properties. Compounds 8-10 were prepared by the route shown below in Scheme 1. (It is noted that the R and subscripted R groups used in the scheme that follows have the meanings shown in the scheme as compared to the prior definitions for superscripted R groups.)

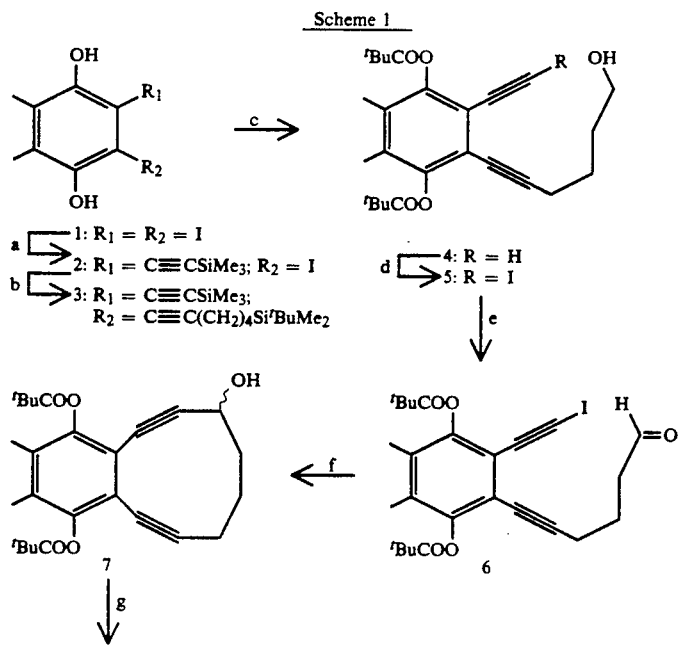

Scheme 1

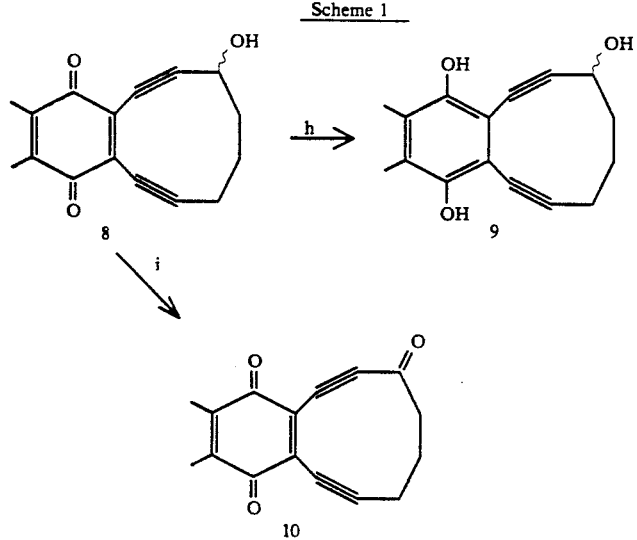

Thus, the readily available diiodide Compound 1 was sequentially coupled With $Me_3SiC\equiv CH$ and $^tBuMe_2Si\text{-}O(CH_2)_4C\equiv CH$ under the catalytic influence of Pd(O)—Cu(I) to afford the diacetylenic Compound 3 via Compound 2 Diiodide Compound 1 was readily prepared from 1,3-dimethylhydroquinone in 82 percent overall yield by bromination followed by iodine exchange. 3.1 Equivalents of $HC\equiv CSiMe_3$, 0.66 equivalents of $(PH_3P)_2PdCl_2$, 0.17 equivalents of CuI and 2.0 equivalents of $^iPr_2NH$ were admixed and reacted with Compound 1 in benzene at 25° C. for 8 hours in step a to form Compound 2 in 58 percent yield. Compound 2 was then reacted in step b with 6 equivalents of $HC\equiv C(CH_2)_4OSi^tBuMe_2$, 0.1 equivalents of $(Ph_3P)_4Pd$, 0.16 equivalents of CuI and 6.5 equivalents of $^iPr_2NH$ in benzene at 25° C. for 13 hours to form Compound 3 in 88 percent yield.

Formation of the bis(pivaloyl) ester of Compound 3 followed by desilylation furnished Compound 4 in 71 percent overall yield as step c. Thus, 10 equivalents of $^tBuCOCl$ in pyridine were reacted with Compound 3 at 60°–65° C. for one hour to quantitatively produce the bis(pivaloyl) ester. That bis ester was then placed in excess $BF_3.OEt_2$ in $CH_2Cl_2$ at 35° C. for 4.5 hours to remove the $SiMe_3$ group. The resulting product was then reacted with tetrabutylammonium fluoride (TBAF) in THF at 25° C. for five minutes to provide Compound 4 in a 71 percent yield for the final two steps.

Iodination of the terminal acetylene of Compound 4 with iodine-morpholine led to iodide Compound 5 which served as a precursor to iodoaldehyde Compound 6. Thus, Compound 4 was reacted in step d with 5.0 equivalents of $I_2$ and excess morpholine in benzene at 45° C. for 40 minutes to provide Compound 5 in 89 percent yield. Compound 6 was prepared in 86 percent yield from Compound 5 in step e by reaction with 2.5 equivalents of PCC in $CH_2Cl_2$ at 25° C. for 1.5 hours.

The crucial ring closure of Compound 6 was carried out with $CrCl_2\text{-}NiCl_2$ system [Takai et al., *J. Am Chem. Soc.*, 108:6048 (1986); and Crevisy et al., *Tetrahedron Lett.*, 32:3171 (1991)] leading to the targeted protected enediyneol Compound 7 in step f. Here, Compound 6 was reacted with 9.0 equivalents of $CrCl_2$ and 0.64 equivalents of $NiCl_2$ in THF at 25° C. for 4.5 hours to provide compound 7 in 75 percent yield.

Compound 7 proved to be quite stable at ambient temperature and was smoothly deprotected in step g by exposure to excess $LiAlH_4$ (in THF at −78°→zero degrees C for ten minutes) to afford, after workup, the quinone Compound 8 in 96 percent yield, presumably through the intermediacy of the air-sensitive hydroquinone Compound 9. Reduction of the thermally labile Compound 8 to the hydroquinone Compound 9 in step h, relatively stable under neutral conditions, was smoothly effected by treatment with saturated aqueous $Na_2S_2O_4$ (91 percent yield). Finally, PCC oxidation (4.0 equivalents PCC, 4Å molecular sieves in $CH_2Cl_2$ at 25° C. for 0.5 hour) of Compound 8 afforded the tricarbonyl Compound 10 in 49 percent yield as step i.

Compound 10 proved to be the most reactive member of the series 7–10 in cycloaromatization studies. Compound 8 was the most potent in cytotoxicity studies.

Cycloaromatization studies with Compound 7–10 using 1,4-cyclohexadiene in toluene revealed the following half lifes: Compound 7 ($t_{\frac{1}{2}}$ = 74 hours at 110° C.); Compound 8 ($t_{\frac{1}{2}}$ = 2.6 hours at 55° C.); Compound 9 (110° C., complicated kinetics due to ease of conversion to Compound 8 even under oxygen extrusion conditions, but seems quite stable prior to oxidation); Compound 10 ($t_{\frac{1}{2}}$ = 32 minutes at 55° C.). These reactions provided Compounds 11–13 as shown schematically in Scheme 2, below.

Scheme 2

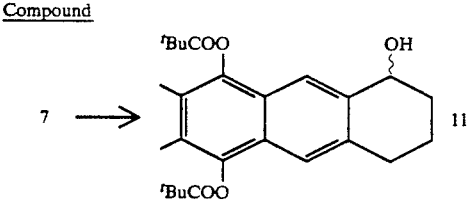

-continued
Scheme 2

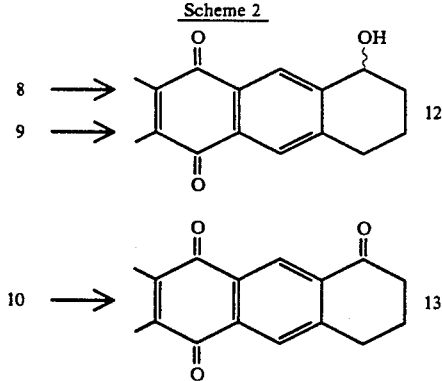

The interaction of Compounds 7-10 and 12 with cell-free supercoiled DNA (φX174) at pH 7.4 and 37° C. is shown in FIG. 1. The stable pivalate derivative Compound 7 exhibited no DNA cleaving activity, whereas Compounds 8, 9 and 10 showed significant DNA damaging properties. It is presumed that, the damage on DNA caused by these agents is at least partly due to their abilities to produce diradical species. Compound 12 exhibited minor activity.

Assayed against a variety of cell lines, these compounds exhibited varying degree of antitumor activity with the most impressive results obtained with Compounds 8 and 10 [e.g. Molt-4 leukemia cells, $IC_{50}$ for Compound 8: $5.0 \times 10^{-7}$M; $IC_{50}$ for Compound 10: $1 \times 10^{-6}$M]. These studies are discussed in greater detail hereinafter.

EXAMPLE 1

Compound 3

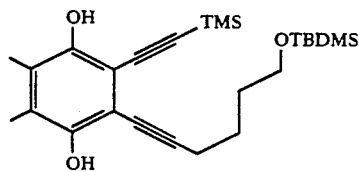

$R_f$: 0.37 (petroleum ether:EtOAc=14:1); 88 percent yield; IR (CCl$_4$) $\nu_{max}$ 3512, 2954, 2857, 2143 cm$^{-1}$; $^1$H NMR (500 MHz, CDCl$_3$) δ5.61, 5.59 (2s, 2H, phenolic OH), 3.67 (t, J=6.6 Hz, 2H, CH$_2$O), 2.56 (t, J=6.6 Hz, 2H, C≡CCH$_2$), 2.18, 2.17 (2s, 6H, 2 aromatic CH$_3$), 1.73-1.71 (m, 4H, CH$_2$CH$_2$), 0.90 (s, 9H, C(CH$_3$)$_3$), 0.28 (s, 9H, Si(CH$_3$)$_3$), 0.06 (s, 6H, 2×CH$_3$ of TBDMS); $^{13}$C NMR (125 MHz, CDCl$_3$) δ 149, 148, 126, 124, 118, 117, 114, 100, 99, 74, 63, 32, 26, 25, 20, 13, 12, 0, −5; HRMS (FAB) calcd for C$_{25}$H$_{44}$O$_3$Si$_2$, 444.2516, found 444.2525.

EXAMPLE 2

Compound 4

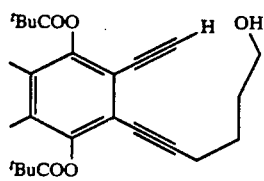

$R_f$: 0.20 (petroleum ether:EtOAc=2:1); 71 percent yield; mp: 119°-120° C.; IR (CCl$_4$) $\nu_{max}$ 3543, 2972, 2871, 1754 cm$^{-1}$; $^1$H NMR (500 MHz, CDCl$_3$) δ 3.66 (t, J=6.5 Hz, 2H, CH$_2$OH), 3.34 (s, 1H, C≡CH), 2.45 (t, J=6.5 Hz, 2H, C≡CCH$_2$), 2.05 (2s, 6H, 2 aromatic CH$_3$), 1.77-1.62 (m, 4H, CH$_2$CH$_2$), 1.40 (s, 18H, 2×C(CH$_3$)$_3$); $^{13}$C NMR (125 MHz, CDCl$_3$) δ 176, 149, 147, 132, 130, 120, 118, 98, 88, 75, 72, 63, 39, 32, 27, 25, 19, 13; HRMS (FAB) calcd for C$_{26}$H$_{34}$O$_5$Cs (M+Cs) 559.1461, found 559.1491; Anal. calcd for C$_{26}$H$_{36}$O$_5$: C, 73.21; H, 8.03; found C, 73.11; H, 8.09.

EXAMPLE 3

Compound 6

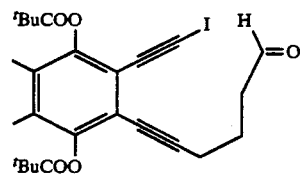

$R_f$: 0.18 (petroleum ether:EtOAc=4:1); 86 percent yield; mp: 126°-127° C.; IR (CCl$_4$) $\nu_{max}$ 2959, 2872, 1757, 1729 cm$^{-1}$; $^1$H NMR (500 MHz, CDCl$_3$) δ 9.87 (s, 1H, CHO), 2.75 (t, J=6.5 Hz, 2H, CH$_2$CHO), 2.50 (t, J=6.5 Hz, 2H, C≡CCH$_2$), 2.05, 2.04 (2s, 6H, 2 aromatic CH$_3$), 1.90 (dddd, J=6.5 Hz, 2H, —CH$_2$—), 1.40, 1.39 (2s, 18H, 2×C(CH$_3$)$_3$); $^{13}$C NMR (125 MHz, CDCl$_3$) δ 202, 176, 149, 147, 132, 131, 120, 119, 97, 89, 85, 76, 43, 39, 27, 21, 19, 13; HRMS (FAB) calcd for C$_{26}$H$_{31}$IO$_5$Cs (M+Cs) 683.0271, found 683.0271.

EXAMPLE 4

Compound 7

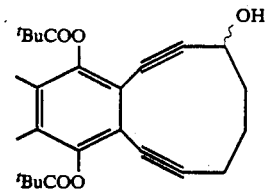

$R_f$: 0.19 (petroleum ether:EtOAc=4:1); 75 percent yield; mp: 185° C. (decomp.); UV (CHCl$_3$) $\lambda_{max}$ (relative intensity) 242 (1.59), 269 (0.78), 314 (0.18) nm; IR (CCl$_4$) $\nu_{max}$ 3400, 2973, 2872, 1755 cm$^{-1}$; $^1$H NMR (500 MHz, CDCl$_3$) δ 4.55 (dd, J=8.9, 4.2 Hz, 1H, CHOH), (2.44-2.42 (m, 2H, C≡CCH$_2$), 2.17-2.10 (m, 2H, CH$_2$CHOH), 2.10 (brs, 6H, 2 aromatic CH$_3$), 1.42, 1.41 (2s, 18H, 2×C(CH$_3$)$_3$); $^{13}$C NMR (125 MHz, CDCl$_3$) δ 176, 146, 145, 131, 130, 122, 121, 104, 102, 81, 78, 63, 39, 38, 27, 24, 21, 13; HRMS (FAB) calcd for C$_{26}$H$_{32}$O$_5$Cs (M+Cs) 557.1304, found 557.1315; Anal. calcd for C$_{26}$H$_{32}$O$_5$: C, 73.56; H, 7.06; found C, 73.55; H, 7.58.

EXAMPLE 5

Compound 8

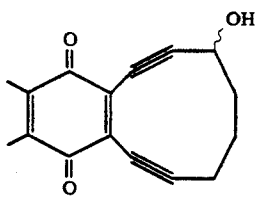

$R_f$: 0.40 (petroleum ether:EtOAc=4:1); 96 percent yield; mp: 80° C. (decomp.); UV (CHCl$_3$) $\lambda_{max}$ (relative intensity) 238 (0.61), 260 (0.64), 298 (1.18), 423 (0.12) nm; IR (CCl$_4$) $\nu_{max}$ 3290, 2935, 2197, 1654 cm$^{-1}$; $^1$H NMR (500 MHz, CDCl$_3$) δ 4.69 (dd, J=8.5, 3.0 Hz, 1H, CHOH), 2.50 (ABqdd, Du=31.3 Hz, J=15.0, 8.5, 2.5 Hz, 2H, C≡CCHH$_2$), 2.27-2.08 (m, 3H, CH$_2$CHOH and one of —CH$_2$—), 2.04 (s, 6H, 2 aromatic CH$_3$), 1.88-1.79 (m, 1H, one of —CH$_2$—); $^{13}$C NMR (125 MHz, CDCl$_3$) δ 182, 141, 138, 137, 129, 116, 111, 81, 79, 63, 37, 23, 22, 13; HRMS (FAB) calcd for C$_{16}$H$_{14}$O$_3$Cs (M+Cs) 386.9997, found 387.0005.

EXAMPLE 6

Compound 9

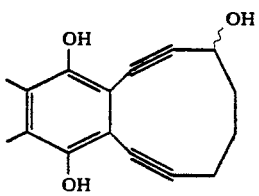

$R_f$: 0.25 (petroleum ether:EtOAc=1:1); 91 percent yield; mp: 185° C. (decomp.); UV (CHCl$_3$) $\lambda_{max}$ (relative intensity) 241 (0.83), 285 (0.32), 347 (0.45) nm; IR (CCl$_4$) $\nu_{max}$ 3042, 2978, 2876 cm$^{-1}$; $^1$H NMR (500 MHz, acetone-d$_6$) δ 7.43, 7.21 (2s, 2H, phenolic OH), 4.53 (ddd, J=8.5, 6.0, 3.0 Hz, 1H, CHOH), 4.29 (d, J=6.0 Hz, 1H, OH), 2.43-2.40 (m, 2H, C≡CCH$_2$), 2.13 (s, 6H, 2 aromatic CH$_3$), 2.13-2.05 (m, 3H, CH$_2$CHOH and one of —CH$_2$—), 1.75-1.67 (m, 1H, one of —CH$_2$—); $^{13}$C NMR (125 MHz, THF-d$_8$) δ 149, 148, 126, 125, 114, 113, 104, 103, 82, 80, 64, 40, 25, 22, 13; HRMS (FAB) calcd for C$_{16}$H$_{16}$O$_3$ 256.1099, found 256.1099.

EXAMPLE 7

Compound 10

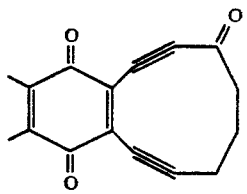

$R_f$: 0.32 (petroleum ether:EtOAc=2:1); 49 percent yield; IR (CCl$_4$) $\nu_{max}$ 2927, 2343, 1680, 1660 cm$^{-1}$; $^1$H NMR (500 MHz, THF-d$_8$) δ 2.85-2.82 (m, 2H, COCH$_2$), 2.74-2.70 (m, 2H, C≡CCH$_2$), 2.20-2.10 (m, 2H, —CH$_2$—), 2.01 (s, 6H, 2 aromatic CH$_3$); MS (EI) 254 (M$^+$ of the cyclized product upon heating), 226, 198, 170, 149, 115.

EXAMPLE 8

Compound 11

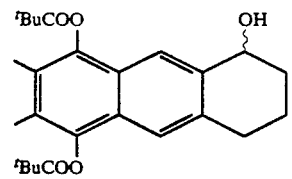

$R_f$: 0.20 (petroleum ether:EtOAc=4:1); 25 percent yield; IR (CCl$_4$) $\nu_{max}$ 3518, 2959, 2871, 1750 cm$^{-1}$; $^1$H NMR (500 MHz, DMSO-d$_6$) δ 7.80, 7.75 (2s, 1H, H-9), 7.29 (s, 1H, H-10), 5.35 (brs, 1H, OH), 4.66 (brs, 1H, CHOH), 2.91-2.80 (m, 2H, H-4), 2.14 (s, 6H, 2 aromatic CH$_3$), 2.00-1.88 (m, 2H, H-2), 1.72-1.63 (m, 2H, H-3), 1.53, 1.52 (2s, 18H, 2×C(CH$_3$)$_3$); HRMS (FAB) calcd for C$_{26}$H$_{34}$O$_5$Cs (M+Cs) 559.1461, found 559.1472.

EXAMPLE 9

Compound 12

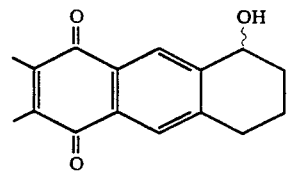

$R_f$: 0.25 (petroleum ether:EtOAc=2:1); 40 percent yield; UV (CHCl$_3$) $\lambda_{max}$ (relative intensity) 226 (0.51), 262 (0.84), 343 (0.11) nm; IR (CCl$_4$) $\nu_{max}$ 3610, 2931, 2874, 1720, 1660 cm$^{-1}$; $^1$H NMR (500 MHz, CDCl$_3$) δ 8.16, 7.79 (2s, 2H, H-9, H-10), 4.86 (t, J=5.0 Hz, 1H, H-1), 2.95-2.80 (m, 2H, H-3), 2.12-1.96 (m, 2H, H-4), 1.95-1.78 (m, 2H, H-3); MS (EI) 256 (M$^+$), 238, 228, 200, 128, 115; HRMS (EI) calcd for C$_{16}$H$_{16}$O$_3$ 256.1099, found 256.1100.

EXAMPLE 10

Compound 13

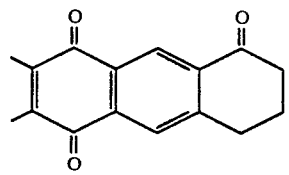

$R_f$: 0.19 (petroleum ether:EtOAc=4:1); 30 percent yield: IR (CCl$_4$) $\nu_{max}$ 1698, 1663, 1552 cm$^{-1}$; $^1$H NMR (500 MHz, CDCl$_3$) δ 8.70, 7.95 (2s, <2H, H-9, H-10), 3.11 (t, J=6.5 Hz, 2H, H-2), 2.74 (t, J=7.0 Hz, 2H, H-4), 2.21-2.15 (m, 8H, H-3 and aromatic CH$_3$); MS (EI) 56, 255, 254 (M$^+$+2, M$^+$+1, M$^+$), 228, 200, 172, 117; HRMS (EI) calcd for C$_{16}$H$_{12}$O$_3$D$_2$ 256.1068, found 256.1074.

EXAMPLE 11

DNA Cleavage Studies

To a vial containing 9 microliters of a cell-free φX174 Type I double-stranded DNA in pH 7.4 50 micromolar Tris-HCl buffer was added 1 microliter of a 1.0 millimolar or other appropriate ethanol solution of Compounds 7, 8, 9, 10 and 12.

The vials were then placed in a 37° C. oven for 15 hours. A 2.0 microliter portion of glycerol loading buffer solution containing bromothymol blue indicator was added to each vial. A 10 microliter aliquot was then drawn from each. Gel electrophoresis analysis of the aliquots was performed using a 1.0 percent agarose gel with ethidium bromide run at 115 volts for one hour. DNA cleavage was indicated by the formation of Type II DNA, which was detected by visual inspection of the gel under 310 nanometer ultraviolet light.

EXAMPLE 12

Screening Against Cancerous Cell Lines

In addition to the DNA cleavage screening already discussed, several of the before-described compounds were screened against a panel of twelve cancerous cell lines as target cells and four "normal" cell preparations. This screening utilized a sulforhodamine B cytotoxicity assay as discussed below.

SULFORHODAMINE B CYTOTOXICITY ASSAY

1. Preparation of target cells in 96-well plates
   a. Drain media from $T_{75}$ flask of target cell line(s) and carefully wash cell monolayer two times with sterile PBS (approximately 5 mL per wash)
   b. Add 5 mL trypsin/EDTA solution and wash monolayer for approximately 15 seconds
   c. Drain all but approximately 1 mL of trypsin/EDTA from flask, cap flask tightly, and incubate at 37° C. for approximately two to five minutes until cells come loose.
   d. Add 10-15 mL tissue culture (T.C.) medium (RPMI 1640 plus 10 percent fetal calf serum and 2 mM L-glutathione) to flask and pipet gently up and down to wash cells.
   e. Remove a 1/2 mL aliquot of the cell suspension and transfer to a glass 12×75 mm culture tube for counting.
   f. Count cells on a hemacytometer using trypan blue, and determine percent viability.
   g. Adjust volume of cell suspension with T.C. media to give a density of $1 \times 10^5$ cells/mL.
   h. Add 100 μL of T.C. medium to wells A1 and B1 of a 96-well plate for blanks.
   i. Add 100 μL of cell suspension to the remaining wells of the 96-well plates.
   j. Incubate plates for 24 hours at 37° C., 5-10 percent $CO_2$ in a humidified incubator.
2. Preparation of sample drugs and toxic control
   a. Stock drug solutions were prepared by dissolving drug in the appropriate solvent (determined during chemical characterization studies) and sterile filtering the drug-solvent solution through a sterile 0.2μ filter unit. An aliquot was taken from each filtered drug solution and the O.D. was measured to determine the drug concentration.
   b. Dilute the stock drug solution prepared above with T.C. medium to the desired initial concentration ($10^{-2}$–$10^{-4}$M). A minimum volume of 220 μL of diluted drug is required per 96-well plate used in the assay.
   c. Prepare toxic control by diluting stock doxorubicin solution to $10^{-7}$ to $10^{-9}$M in T.C. medium. A minimum volume of 300 μL is required per 96-well plate.
3. Addition of Sample Drugs, Compounds and Controls to 96-well Plates
   a. Remove and discard 100 μL of T.C. medium from the wells in Column #2 of the 96-well plate using a multi-channel pipettor and sterile tips.
   b. Add 100 μL of the initial compound dilution to adjacent duplicate wells in Columns #2. (Four materials can be tested in duplicate per 96-well plate.)
   c. Remove 10 μL of diluted compound from the wells in Column #2 and transfer to the corresponding wells in Column #3. Mix by pipetting up and down gently approximately five times.
   d. Transfer 10 μL to the appropriate wells in Column #4 and continue to make 1:10 dilutions of compound across the plate through Column #12.
   e. Remove and discard 100 μL of medium from wells F1, G1, and H1. Add 100 μL of toxic control (Doxorubicin diluted in T.C. medium) to each of these wells.
   f. Incubate (37° C., 5-10 percent $CO_2$ in humidified incubator) plates for a total of 72 hours. Check plates at 24 hour intervals microscopically for signs of cytotoxicity.
4. Cell Fixation
   a. Adherent cell lines:
      1. Fix cells by gently layering 25 μL of cold (4° C.) 50 percent trichloroacetic acid (TCA) on top of the growth medium in each well to produce a final TCA concentration of 10 percent.
      2. Incubate plates at 4° C. for one hour.
   b. Suspension cell lines:
      1. Allow cells to settle out of solution.
      2. Fix cells by gently layering 25 μL of cold (4° C.) 80 percent TCA on top of the growth medium in each well.
      3. Allow cultures to sit undisturbed for five minutes.
      4. Place cultures in 4° C. refrigerator for one hour.
   c. Wash all plates five times with tap water.
   d. Air dry plates.
5. Staining Cells
   a. Add 100 μL of 0.4 percent (wt./vol.) Sulforhodamine B (SRB) dissolved in 1 percent acetic acid to each well of 96-well plates using multichannel pipettor.
   b. Incubate plates at room temperature for 30 minutes.
   c. After the 30 minute incubation, shake plates to remove SRB solution.
   d. Wash plates two times with tap water and 1× with 1 percent acetic acid, shaking out the solution after each wash. Blot plates on clean dry absorbent towels after last wash.
   e. Air dry plates until no standing moisture is visible.
   f. Add 100 μL of 10mM unbuffered Tris base (ph 10.5) to each well of 96-well plates and incubate for five minutes on an orbital shaker.
   g. Read plates on a microtiter plate reader at 540 nM.

$IC_{50}$ values; i.e., the concentration of Compound required to kill one-half of the treated cells, where then calculated.

The cell lines assayed are listed below along with their respective sources:

| Cell Type | Cell Line |
|---|---|
| Human Mammary Epithelial Cells | HMEC |
| Normal Human Dermal Fibroblast | NHDF |
| Normal Human Epidermal Keratinocytes | NHEK |
| Chinese Hamster Ovary | CHO |
| Cancer Cell Lines | |
| Melanoma | SK-Mel-28 |
| Ovarian Carcinoma | Ovcar-3 |
| Cervical Carcinoma | SIHA |
| Breast Carcinoma | MCF-7 |
| Renal Carcinoma | 786-0 |
| Lung Carcinoma | H-322 |
| Lung Carcinoma | UCLA P-3 |
| Colon Carcinoma | HT-29 |
| Pancreatic Carcinoma | Capan-1 |
| Mouse Leukemia | P-388 |
| Promyeocytic Leukemia | HL-60 |
| T-Cell Leukemia | Molt-4 |

UCLA P-3 cells were provided by Dr. R. Reisfeld of The Scripps Research Institute, and were originally obtained from Dr. D. Morton, University of California, Los Angeles. P-3 is a human non-small cell lung carcinoma cell line. HMEC, NHDF and NHEK cells were obtained from Clonetics Corporation, San Diego, CA. All other cells or cell lines were obtained from the American Type Culture Collection (ATCC) (all except CHO cells are human or mouse cancer cell lines as described by the ATCC).

Separate control studies were also carried out using the following well known anticancer drugs with the following IC$_{50}$ values for NHDF and cancer cells.

| Drug | Range of Average IC$_{50}$ Values (Molarity) | |
|---|---|---|
| | NHDF | Cancer Cells |
| Doxorubicin | — | $1.6 \times 10^{-10}$-$9.8 \times 10^{-8}$ |
| Dynemicin A | $10^{-8}$ | $1.6 \times 10^{-8}$-$9.8 \times 10^{-10}$ |
| Calicheamicin | $2.5 \times 10^{-9}$ | $5 \times 10^{-5}$-$10^{-12*}$ |
| Morpholinodoxorubicin | — | $1.6 \times 10^{-7}$-$9.8 \times 10^{-9}$ |
| Taxol | $10^{-8}$ | $10^{-7}$-$10^{-9}$ |
| Methotrexate | $5 \times 10^{-5}$ | $>10^{-4}$-$10^{-8}$ |
| Cis-Platin | $5 \times 10^{-5}$ | $10^{-4}$-$10^{-6}$ |
| Melphelan | $10^{-4}$ | $10^{-4}$-$10^{-6}$ |

* Molt-4 cells were susceptible at $10^{-12}$M. All other cells were susceptible at $3.9 \times 10^{-9}$M or higher concentrations.

| CYTOTOXICITY OF COMPOUNDS 7-10 AGAINST VARIOUS CELLS | | | | |
|---|---|---|---|---|
| | IC$_{50}$ Values for Compound Numbers* | | | |
| CELLS | 7 | 9 | 8 | 10 |
| Normal | | | | |
| NHDF | 1e-4 | 2.5e-5 | 3.1e-6 | 1e-4 |
| HMEC | 1e-4 | 2.5e-5 | 3.1e-6 | 1e-4 |
| NHEK | 2.5e-5 | 1.3e-5 | 3.1e-6 | 1e-4 |
| CHO | 1e-4 | 1.3e-5 | 3.2e-6 | 1e-4 |
| Cancerous | | | | |
| SK-Mel-28 | 1e-4 | 2.5e-5 | 6.3e-6 | 1e-4 |
| CAPAN-1 | 1.3e-5 | 1.3e-5 | 3.1e-6 | 1e-4 |
| H322 | 1e-4 | 2.5e-5 | 1.3e-5 | 1e-4 |
| UCLA P-3 | 1.3e-5 | 2.5e-5 | 6.3e-6 | 5e-5 |
| MCF-7 | 5e-5 | 2.5e-5 | 6.3e-6 | 1.3e-5 |
| OVCAR-3 | 1.3e-5 | 2.5e-5 | 6.3e-6 | 2.5e-5 |
| HT-29 | 1.3e-5 | 2.5e-5 | 6.3e-6 | 5e-5 |
| SIHA | — | — | — | 1.3e-5 |
| 786-0 | — | — | — | 5e-5 |
| HL-60 | 1e-4 | 1.6e-6 | 7.8e-6 | 2.5e-5 |
| MOLT-4 | 1e-4 | 5e-5 | 1e-7 | 1.19e-6 |
| p-388 | 1.3e-5 | 3.1e-6 | 2e-6 | — |

*IC$_{50}$ values are expressed as molarity. The abbreviation "e" is used for an exponent power of ten rather than a natural log. Thus "1e-5" is "$1 \times 10^{-5}$M", etc.

As is seen from the above data, Compounds 8 and 10 exhibited cytotoxicity potencies against cancer cells similar to those of methotrexate, cis-Platin and melphelan. Compound 8 was similarly toxic to the normal NHDF and cancer cells except Molt-4 cells, whereas Compound 10 was less toxic than those well known anticancer drugs against the NHDF cells.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A compound of the formula

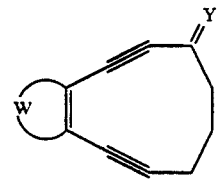

wherein =Y is =O or —OH and —H, and

W together with the carbon atoms of the depicted, intervening vinylene group forms a benzoquinoidal, naphthoquinoidal or anthraquinoidal ring system or the corresponding hydroquinoidal form thereof, with the proviso that when W forms a corresponding hydroquinoidal ring system, =Y is —OH are —H.

2. The compound of claim 1 wherein W together with the carbon atoms of the depicted, intervening vinylene group forms a benzoquinoidal or hydroquinoidal ring system.

3. The compound of claim 1 wherein the benzoquinoidal, naphthoquinoidal or anthraquinoidal ring system or corresponding hydroquinoidal form thereof is substituted with a C$_1$-C$_6$ alkyl or C$_1$-C$_6$ alkoxy group.

4. The compound of claim 1 wherein =Y is =O.

5. The compound of claim 1 wherein =Y is —OH and —H.

6. A compound selected from the group consisting of Formulas II and III, below,

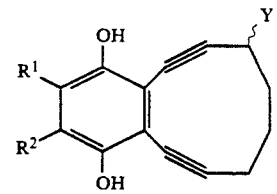

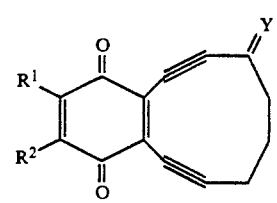

wherein =Y is =O or —OH and —H, and

R$^1$ and R$^2$ are the same or different and are selected from the group consisting of hydrogen, C$_1$-C$_6$ alkyl and C$_1$-C$_6$ alkoxy.

7. The compound of claim 6 wherein R$^1$=R$^2$.

8. The compound of claim 7 wherein R$^1$ is a C$_1$-C$_6$ alkyl group.

9. The compound of claim 8 wherein said C$_1$-C$_6$ alkyl group is methyl.

10. A compound having a structural formula selected from the group consisting of those shown below

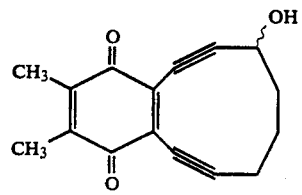

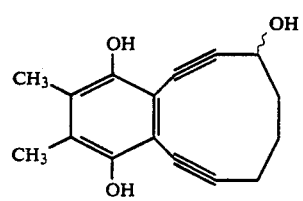

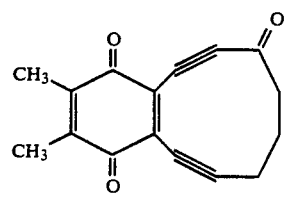

11. A composition comprising a physiologically tolerable diluent having an active agent dissolved or dispersed therein in a DNA cleaving amount, said active agent being a compound of the formula

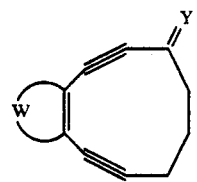

wherein =Y is =O or —OH and —H, and
W together with the carbon atoms of the depicted, intervening vinylene group forms a benzoquinoidal, naphthoquinoidal or anthraquinoidal ring system or the corresponding hydroquinoidal form thereof, with the proviso that when W forms a corresponding hydroquinoidal ring system, =Y is —OH and —H.

12. The composition of claim 11 wherein the benzoquinoidal, naphthoquinoidal or anthraquinoidal ring system or corresponding hydroquinoidal form thereof is substituted with a $C_1$-$C_6$ alkyl or $C_1$-$C_6$ alkoxy group.

13. The composition of claim 11 wherein W together with the carbon atoms of the depicted, intervening vinylene group forms a benzoquinoidal or hydroquinoidal ring system.

14. The composition of claim 13 wherein said active agent is a compound of Formula II or III, below

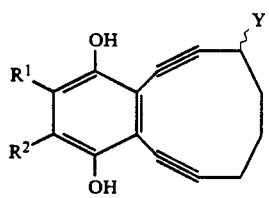

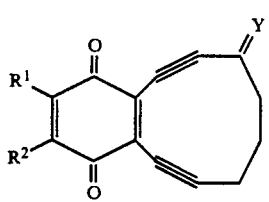

wherein =Y is =O or —OH and —H, and
$R^1$ and $R^2$ are the same or different and are selected from the group consisting of hydrogen, $C_1$-$C_6$ alkyl and $C_1$-$C_6$ alkoxy.

* * * * *